United States Patent
Carroll et al.

(10) Patent No.: US 9,232,809 B2
(45) Date of Patent: Jan. 12, 2016

(54) RAPIDLY DISSOLVING COMESTIBLE SOLID

(71) Applicant: THE HERSHEY COMPANY, Hershey, PA (US)

(72) Inventors: Thomas J. Carroll, Mechanicsburg, PA (US); Steven M. Kumiega, Hummelstown, PA (US)

(73) Assignee: The Hershey Company, Hershey, PA (US)

( * ) Notice: Subject to any disclaimer, the term of this patent is extended or adjusted under 35 U.S.C. 154(b) by 0 days.

(21) Appl. No.: 14/666,505

(22) Filed: Mar. 24, 2015

(65) Prior Publication Data

US 2015/0289537 A1    Oct. 15, 2015

Related U.S. Application Data

(63) Continuation of application No. 13/705,542, filed on Dec. 5, 2012, now Pat. No. 9,023,414.

(60) Provisional application No. 61/568,273, filed on Dec. 8, 2011.

(51) Int. Cl.
*A23G 3/50* (2006.01)
*A23G 3/34* (2006.01)

(52) U.S. Cl.
CPC ............... *A23G 3/50* (2013.01); *A23G 3/0061* (2013.01); *A23V 2002/00* (2013.01)

(58) Field of Classification Search
USPC .................................................... 426/5, 548
See application file for complete search history.

(56) References Cited

U.S. PATENT DOCUMENTS

| | | | |
|---|---|---|---|
| 5,098,730 A * | 3/1992 | Pepper et al. | 426/548 |
| 5,869,098 A | 2/1999 | Misra et al. | |
| 2006/0257551 A1 | 11/2006 | Huzinec et al. | |
| 2007/0154592 A1 | 7/2007 | Dauchy et al. | |
| 2009/0007903 A1 | 1/2009 | Duflot et al. | |
| 2011/0159143 A1 | 6/2011 | Elejalde et al. | |

FOREIGN PATENT DOCUMENTS

| | | |
|---|---|---|
| DE | 4411582 A1 | 10/1995 |
| EP | 0370761 A2 | 5/1990 |
| FR | 2786665 A1 | 6/2000 |
| JP | 2010259334 A | 11/2010 |
| WO | 94/21827 A | 9/1994 |
| WO | 98/12932 A | 4/1998 |
| WO | 2011026003 A2 | 3/2011 |

* cited by examiner

*Primary Examiner* — Walter Webb
(74) *Attorney, Agent, or Firm* — McNees Wallace & Nurick LLC

(57) ABSTRACT

A rapidly dissolving comestible solid is disclosed that includes a fondant formed from a super saturated solution having a bulk sweetener, a hydrocolloid, a texturizing agent, and water. Other ingredients may also be added, and in embodiments in which the solid is provided as a breath freshener, flavoring agents, cooling agents and/or other ingredients useful in conventional breath freshening products may be used. A method for making the comestible solid is also disclosed.

16 Claims, 2 Drawing Sheets

RAPIDLY DISSOLVING COMESTIBLE SOLID

RELATED APPLICATIONS

This application is a Continuation of application Ser. No. 13/705,542, filed Dec. 5, 2012, entitled RAPIDLY DISSOLVING COMESTIBLE SOLID, which claims the benefit of and priority to U.S. Application No. 61/568,273 filed Dec. 8, 2011, which are hereby incorporated by reference in their entirety.

FIELD

This application is directed to comestibles and more particularly to rapidly dissolving comestible solids.

BACKGROUND

Mints and chewing gum are commonly used by consumers to freshen breath after meals, before personal interactions, and in other social situations. While these products are generally effective, there are many situations in which a consumer desires fresh breath but doesn't have time for a traditional tablet mint to dissolve or to chew gum long enough to achieve the desired level of freshness.

Mouthwash is a quick and effective way to freshen one's breath, but is generally not a suitable alternative in most cases for a variety of reasons. Another manner of providing a quicker way in which to achieve freshness has been the use of products generally known as breath strips, which are dissolvable films containing breath freshening ingredients. Breath strips have their own attendant drawbacks, including a propensity to stick to the roof of one's mouth and a mouthfeel that some consumers find unpleasant. Breath strips can sometimes also start to become sticky and/or dissolve on contact with the skin when removed from their container, particularly in humid weather.

These and other drawbacks are found in current breath fresheners and other products.

SUMMARY

What is needed is a comestible product that provides a tactile shape and mouthfeel consistent with a traditional tablet mint but that has a rapid dissolution that is more characteristic of a breath strip, to which exemplary embodiments are directed.

According to an exemplary embodiment, a rapidly dissolving comestible solid comprises a fondant of a super saturated solution of a bulk sweetener, a texturizing agent and, optionally, a hydrocolloid, wherein the fondant has a crystalline structure that does not exhibit cold flow at room temperature.

According to another exemplary embodiment, a method of making a rapidly dissolving comestible solid comprising mixing a bulk sweetener, a texturizing agent and a hydrocolloid in water to form a solution; cooking the solution to a temperature in the range of about 280° F. to about 300° F. to form a fondant; cooling the fondant to a temperature in the range of about 100° F. to about 150° F. to initiate crystal formation; extruding the fondant into a sheet; optionally applying indicia on the fondant; cutting the sheet of fondant; curing the fondant; and breaking the fondant into pieces.

An advantage of certain embodiments is that a comestible product is provided that has a tactile shape and mouthfeel consistent with a traditional tablet mint but that dissolves much more rapidly.

Another advantage is that the comestible product is made of a fondant that does not exhibit cold flow at room temperature, resulting in a stand-alone fondant product that does not require a shell or other support to retain its shape.

Still another advantage of certain embodiments is that the comestible products in accordance with exemplary embodiments can be manufactured according to either a batch or a continuous process.

These and other features and advantages of the present invention will be apparent from the following more detailed description of exemplary embodiments which, along with the drawings, illustrate by way of example the principles of the invention.

DETAILED DESCRIPTION OF EXEMPLARY EMBODIMENTS

Figure 1:
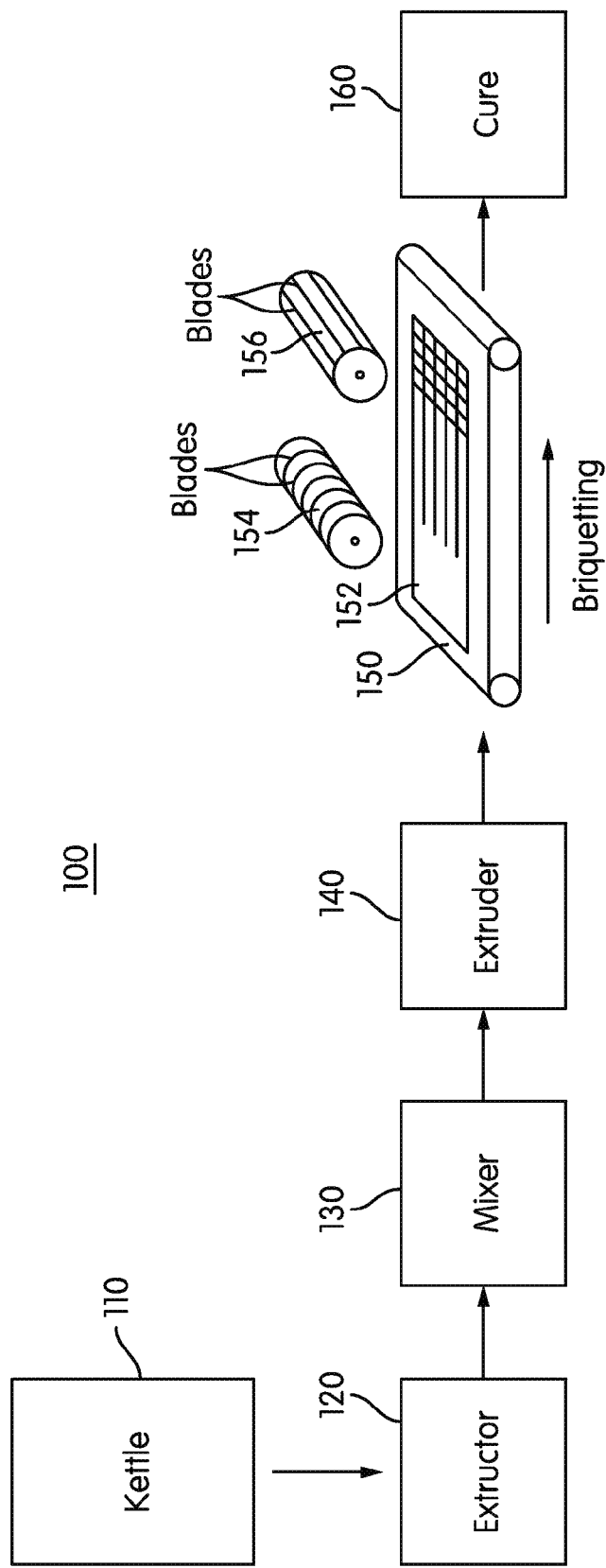
FIG. 1 schematically illustrates a method for making a product in accordance with an exemplary embodiment of the invention.

Exemplary embodiments are directed to a rapidly dissolving comestible solid that includes a super saturated solution comprising a bulk sweetener, an optional hydrocolloid, a texturizing agent, and water. Other ingredients may also be added, and in embodiments in which the solid is provided as a breath freshener, flavoring agents, cooling agents and/or other ingredients useful in conventional breath freshening products may be used.

The super saturated solution may also be referred to as a fondant. Fondants are supersaturated solutions typically used as topicals for decorating cakes, pastries and confections and in most cases have been sugar-based. Fondants have previously been used as fillings or centers for various confections, including in chewing gums. However, prior fondants were incapable of being used as an independent product for a variety of reasons, including that conventional fondants don't hold their shape or readily solidify. In many cases, those conventional fondants had to be positioned between two layers of another structure such as a laminated chewing gum.

The inventors have discovered fondants formulated to achieve a stand-alone solid product that can retain its form (i.e., does not exhibit cold flow at room temperature), looks and feels like a tablet mint, and that dissolves rapidly.

The comestible solids formed in accordance with exemplary embodiments are super saturated solutions that prior to cooking typically comprise in the range of about 68% to about 75%, typically about 68% to about 72%, by weight bulk sweetener, about 15% to about 25% by weight texturizing agent, 0% to about 3.0%, typically about 1.0% to about 2.5%, by weight hydrocolloids, along with up to about 10% by weight water. Flavoring agents, sensates and other additives may also be added depending on a particular flavor or sensation to be imparted.

The post-processing moisture content of the final comestible solid product formed in accordance with exemplary embodiments is about 3% to about 6% by weight, preferably about 4% to about 5% by weight. The comestible solid products also have a post-processing water activity in the range of about 0.40 to 0.67, more typically between 0.50 and 0.60 and preferably between 0.52 and 0.57.

The crystal structure in the formed comestible solid product is sufficient to retain its shape and still maintain a soft and creamy dissolvable texture. This can be achieved by crystals having a median particle size of less than about 100 microns when measured by SEM or polarized light. Typically, the median particle size is about 50 microns.

The crystal structure in the formed solid may be controlled by cook temperature, choice of bulk sweetener, mixing speed and through the addition of hydrocolloids and texturizing agents. The product's mouthfeel may also be controlled by moisture content in addition to variables that affect crystal structure, such as the amount of bulk sweetener and texturizing agents. As a result, exemplary embodiments are produced to have extremely fast dissolving qualities and good meltability, but while still maintaining a specific shape without the need for a form-containing package or mold. Texture can be further imparted through the use of the hydrocolloids that also modify the degree of crystallization.

Preferably, the super saturated solutions of exemplary embodiments are xylitol-based, i.e., employ xylitol as the bulk sweetener. It will be appreciated, however, that in some cases other intense sweetening agents may also be used in combination with xylitol, such as acesulfam-K, aspartame, sucralose, neotame, and stevia, by way of example.

The texturizing agent is typically sugar-free and preferably is or contains maltitol syrup. One example of a suitable texturizing agent is a moisture-reduced maltitol syrup such as that sold under the tradename Lycasin 85/55 available from Roquette. Other suitable texturizing agents may also be used, such as polyglycitol syrups for example. Polyglycitol syrups can vary in the degree of polymerization.

The hydrocolloid is an optional component, but is preferably included. The hydrocolloid may be any edible hydrocolloid or a combination of such hydrocolloids may be employed. The hydrocolloids are selected to contribute to a smooth texture and enhance or retard the meltaway textures in the product, but without affecting the solid's ability to take on a free standing shape. Preferably, the hydrocolloid is a cellulose derivative such as carboxy methyl cellulose (CMC). Other suitable hydrocolloids include hydroxy-propyl methyl cellulose (HPMC), other cellulose derivatives, agar-agar, carrageenan, gelatin powder, pectin, xanthan gum, gum arabic, guar gum, locust bean gum, alginate and starch.

The molecular weight of the hydrocolloid and accordingly its viscosity modification properties may vary depending upon the particular characteristics desired, including the dissolution profile of the comestible solid. For example, if CMC is used as the hydrocolloid it may be a low viscosity (e.g., Ticalose 15), moderate viscosity (e.g., Ticalose 2500), or high viscosity (e.g., Ticalose 6000) or some combination of CMC ingredients to achieve the desired viscosity. The particular viscosity desired may vary depending upon the characteristics of the particular product to be formed; higher viscosities tend to slow the dissolution rate of the formed product and increase its pliability and chewiness. Regardless of the hydrocolloid viscosity, the overall weight percentage of the hydrocolloid prior to cooking is up to about 3.0% as previously described.

Figure 2:
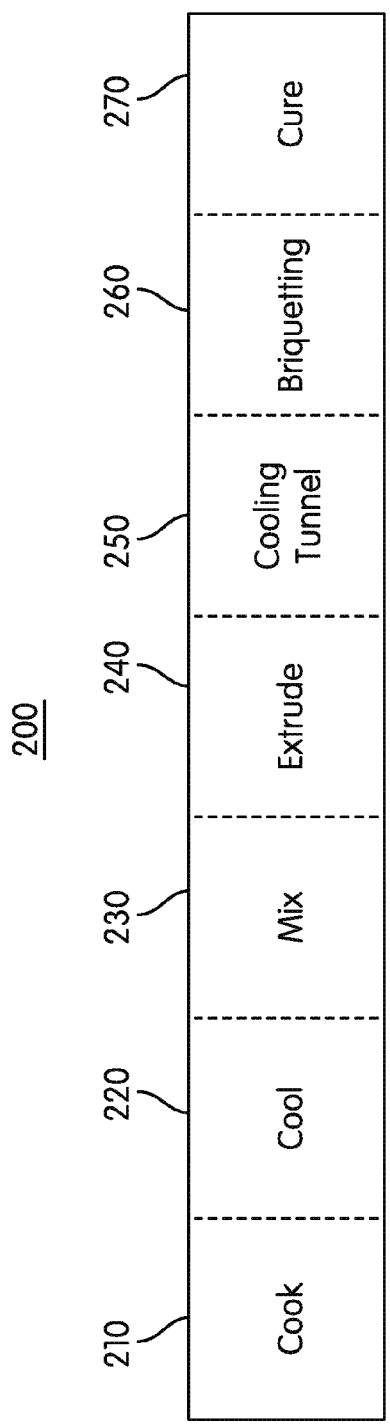
FIG. 2 schematically illustrates another method for making a product in accordance with an exemplary embodiment of the invention.

The comestible solids produced in accordance with exemplary embodiments may be produced either by a batch process 100 as shown in FIG. 1 or by a continuous process 200 as shown in FIG. 2.

In either case, the process involves cooking the basic fondant ingredients, which are mixed and cooked to form a homogenous viscous solution, preferably with no visual signs of sweetener crystals or undissolved hydrocolloids. For embodiments in which the sweetener is xylitol, the solution should be cooked until it forms a fondant and reaches a temperature in the range of about 280° F. to about 300° F., preferably in the range of about 290° F. to about 295° F., which is useful in achieving the desired level of crystallinity in the finished product. The cooked fondant is thereafter cooled to a temperature in the range of about 100° F. to about 150° F. and held for a period of time sufficient to initiate crystal growth, preferably in the range of about 120° F. to about 130° F. for a batch process and higher for a continuous process.

In the batch process 100 of FIG. 1, the cooking typically occurs in a kettle 110 as a discrete step, after which the fondant may thereafter be blocked off and optionally fully solidified and stored at room temperature. Even in the continuous process 200 shown in FIG. 2, the fondant may be blocked off after the step of cooking 210 prior to the remaining steps being carried out in a continuous manner. For batch processes, the solidified fondant subsequently can be delivered to an extructor 120, where it is softened under high torque for further processing. Once suitably softened, the fondant can be dispatched to a mixer 130.

In the mixer 130, the fondant is stirred at a temperature in the range of about 80° F. to about 120° F. Also in the mixer 130, flavoring and/or sensates may be added. In exemplary embodiments in which the rapidly dissolving comestible solids are mint products, common flavorings include flavor oils such as spearmint oil, oil of wintergreen (methylsalicylate) and/or peppermint oil, although any kind or type of flavoring may be added. Furthermore, flavorings are not limited to flavor oils, but may be solvent-based, spray-dried, crystalline additives, encapsulated or any other type of flavoring used with comestible products. Such crystalline additives may contain food approved FDA dyes or aluminum lakes for added visual impact. Similarly, sensates may include one or more of those known sensates that deliver a cooling sensation, such as menthol by way of example only. The use of such ingredients in combination with the characteristics of fondant provide a comestible solid that can deliver an intense freshening/cooling sensation in combination with a soft, creamy mouthfeel. It will be appreciated that other flavorings and sensates may also be employed if other taste effects are sought to be achieved.

The fondant is discharged from the mixer 130 generally at a temperature less than or equal to 120° F. The fondant may be discharged via an extruder 140 or is otherwise fed to such a device, so that the fondant is formed into thin sheets 152. In one embodiment, the fondant is formed into a sheet 152 with a thickness of about 0.200 inches, although larger or smaller thicknesses may be used.

Once formed into sheets 152, the fondant may be slightly cooled upon leaving the extruder 140, upon which the fondant sheets 152 can thereafter be formed into individual pieces. The formation of individual pieces may take place by a briquetting process in which the fondant sheets 152 are passed on a conveyor 150 through rollers 154, 156 having knife blades formed on them, followed by curing in which the scored, cured sheets 152 are broken into the individual pieces. The individual pieces can be formed into any size, but are ordinarily on scale with the size of a conventional mint; i.e., are small enough so that one or more individual pieces can be consumed whole.

The briquetting process is generally one that is well understood within the art as a method of forming smaller pieces of a confectionery or other food product from a larger sheet of material. However, in exemplary embodiments the order of briquetting is preferably reversed from conventional processes. That is, the fondant sheets 152 passed through the rollers 154, 156 are preferably first scored by a roller 154 having scoring knives that form cuts in a direction parallel to the fondant sheet movement through the rollers. Thereafter, a second cut is made by passing the scored sheets through a roller 156 having axial knives to make a cut perpendicular to sheet movement. The roller knives 154, 156 score the sheet but do not necessarily make a complete cut and it may be beneficial for the sheets to be subsequently broken apart into individual pieces later in the manufacturing process after curing.

It may be desirable to apply indicia to the product, which can be accomplished, for example, by embossing using a suitable die corresponding to whatever shape, letter, symbol or other indicia to be imparted. Embossing may occur at any point following extrusion, but preferably takes place after at least some cooling has occurred; if the embossing occurs while the product is warm, the embossed indicia may have a tendency to collapse via cold flow. Other methods of imparting indicia may also be used including debossing, printing (e.g., laser, gravure, off-set, etc.), stamping and other methods known for forming indicia on an edible product.

Following briquetting and any embossing or other application of indicia, the product may be subjected to a curing step 160, which is typically carried out in a conditioned environment having a temperature in range of about 60° F. to about 70° F., preferably about 65° F., and a relative humidity of about 25% to about 45% for a suitable period of time, typically in the range of about twelve to about twenty-four hours, although shorter or longer times may be employed. The scored sheets 152 can then be broken into individual pieces along the score lines previously formed and the pieces packaged. Prior to packaging, the product may be dusted with a non-hygroscopic powder such as mannitol or other fine edible powder to aid in keeping pieces from sticking together in the package. Preferably, the product is not coated with a candy or other crunchy shell, which would impede the rapid dissolution of the formed product. However, the product may be film coated to minimize moisture pickup and enhance stability for increased shelf-life.

In the continuous process 200, illustrated schematically in FIG. 2, the fondant is cooked 210 and cooled 220 as previously described to initiate crystal formation. The fondant is then fed directly to a mixer, which may be a downstream mixer in another part of the same machine used to cook the fondant, where it is mixed (stirred) 230 and further cooled to about 80° F. to about 120° F. and flavorings and/or sensates are added.

The fondant is then extruded 240 into sheets and directed through a cooling tunnel 250 in a conditioned environment typically having a temperature of about 45° F. and a relative humidity of about 35%. The sheets are briquetted 260 in the manner described with respect to FIG. 1 and optionally imparted with indicia also in a manner similar to that described for the batch process.

Figure 3:
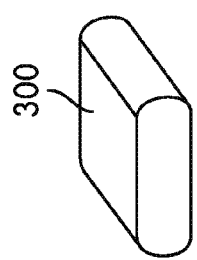
FIG. 3 illustrates a comestible solid in accordance with an exemplary embodiment.

Thereafter, the continuous process continues to be carried out in the same or similar fashion as the batch process, including the steps of curing, breaking, optional dusting and packaging to produce a rapidly dissolving comestible solid in accordance with exemplary embodiments. FIG. 3 illustrates a rapidly dissolving comestible solid formed in accordance with exemplary embodiments.

EXAMPLES

The invention is further described in the context of the following examples, which are presented by way of illustration, not of limitation.

Example 1

A fondant was prepared by dissolving 70% by weight xylitol, 20.4% by weight maltitol syrup (Lycasin 85/55 from Roquette) as the texturizing agent, and 1% by weight CMC (Ticalose 15 from TIC Gums) as the hydrocolloid in 8.6% by weight water, which was cooked to 293° F. The fondant was extruded, sheeted, and formed in accordance with the batch process described above. The finished product had a moisture content of 4.4% and a water activity (Aw) of 0.57; it held its shape and had a firm tactile feel with good dissolvability.

Example 2

A fondant was prepared by dissolving 70% by weight xylitol, 20.4% by weight maltitol syrup (Lycasin 85/55 from Roquette) as the texturizing agent, and 1% by weight CMC (Ticalose 2500 from TIC Gums) as the hydrocolloid in 8.6% by weight water, which was cooked to 293° F. The fondant was extruded, sheeted, and formed in accordance with the batch process described above. The finished product had a moisture content of 4.1% and a water activity (Aw) of 0.54; it held its shape, but was pliable and exhibited good dissolvability.

Example 3

A fondant was prepared by dissolving 70% by weight xylitol, 20.4% by weight maltitol syrup (Lycasin 85/55 from Roquette) as a texturizing agent and 1% by weight CMC (Ticalose 6000 from TIC gums) as the hydrocolloid in 8.6% by weight water, which was cooked to 293° F. The fondant was extruded, sheeted, and formed in accordance with the batch process described above. The finished product had a moisture content of 5.1% and a water activity (Aw) of 0.53; it held its shape, but was pliable and exhibited good dissolvability.

Example 4

A fondant was prepared by dissolving 69% by weight xylitol, 20.4% by weight maltitol syrup (Lycasin 85/55 from Roquette) as a texturizing agent and a total of 2% by weight CMC (1% by weight Ticalose 2500 and 1% by weight Ticalose 15, both from TIC gums) as the hydrocolloid in 8.6% by weight water, which was cooked to 293° F. The fondant was extruded, sheeted, and formed in accordance with the batch process described above. The finished product had a moisture content of 4.74% and a water activity (Aw) of 0.55; it held its shape, but was pliable and exhibited good dissolvability.

Example 5

A fondant was prepared by dissolving 68.5% by weight xylitol, 20.4% maltitol syrup (Lycasin 85/55 from Roquette) as a texturizing agent and a total of 2.5% by weight CMC (1% by weight Ticalose 2500 and 1.5% by weight Ticalose 15, both from TIC gums) as the hydrocolloid in 8.6% by weight water, which was cooked to 293° F. The fondant was extruded, sheeted, and formed in accordance with the batch process described above. The finished product had a moisture content of 4.61% and a water activity (Aw) of 0.53; it held its shape, but was pliable and exhibited good dissolvability.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A comestible solid comprising a bulk sweetener, a texturizing agent and a hydrocolloid, wherein the solid is a fondant formed of a supersaturated solution having a post-processing moisture content of less than 6% by weight and a crystalline structure that does not exhibit cold flow at room temperature and having a median crystalline particle size of about 50 microns up to about 100 microns.

2. The comestible solid of claim 1 further comprising flavoring agents, sensates, or combinations thereof.

3. The comestible solid of claim 1, wherein the comestible solid has a post-processing moisture content of about 3% to about 6% by weight.

4. The comestible solid of claim 1, wherein the comestible solid has a post-processing water activity in the range of about 0.40 to about 0.60.

5. The comestible solid of claim 1 further comprising a coating surrounding the comestible solid.

6. The comestible solid of claim 5, wherein the coating is a film coating.

7. The comestible solid of claim 1, wherein the texturizing agent is selected from the group consisting of maltitol syrup, polyglycitol syrup, and combinations thereof.

8. The comestible solid of claim 1, wherein the hydrocolloid is selected from the group consisting of carboxy methyl cellulose, hydroxy-propyl-methyl cellulose, cellulose derivatives, agar-agar, carrageenan, pectin, xanthan gum, gum arabic, guar gum, locust bean gum, alginate, starch, and combinations thereof.

9. The comestible solid of cliam 1, comprising a pre-processing composition of about 15% to about 25% by weight texturizing agent and up to about 3.0% by weight hydrocolloid.

10. A method of making a comestible solid comprising mixing a bulk sweetener, a texturizing agent and a hydrocolloid in water; thereafter cooking the mixture to a viscous, homogenous super saturated solution having no visible bulk sweetener crystals or undissolved hydrocolloids to form a fondant; thereafter cooling the fondant to initiate crystal growth;

forming the fondant into pieces; and curing the fondant to a moisture content of less than 6% by weight, the resulting fondant pieces having a crystalline structure that does not exhibit cold flow at room temperature.

11. The method of claim 10, wherein the step of cooking comprises cooking at a temperature in the range of about 280° F. to about 300° F.

12. The method of claim 10, wherein the step of cooling comprises cooling the fondant to a temperature in the range of about 100° F. to about 150° F.

13. The method of claim 10, wherein the step for forming the fondant into pieces comprises extruding the fondant into a sheet and cutting the sheet into pieces.

14. The method of claim 13, wherein the step of cutting the sheet of fondant comprises briquetting the sheet of fondant by moving the sheet relative to a plurality of knife blades to score the sheet in a direction parallel to sheet movement followed by scoring the sheet in a direction perpendicular to sheet movement.

15. The method of claim 10, further comprising adding a sensate, a flavoring, or a combination thereof after the cooking step.

16. The method of claim 10, wherein the step of curing comprises curing the fondant in a conditioned environment having a temperature in the range of about 60° F. to about 70° F. and relative humidity in the range of about 25% to about 45%.

* * * * *